United States Patent
Shi et al.

(10) Patent No.: US 9,688,646 B2
(45) Date of Patent: Jun. 27, 2017

(54) PROCESS FOR PRODUCING N-METHYL OR N,N-DIMETHYL AMINES

(71) Applicant: Lanzhou Institute of Chemical Physics, Chinese Academy of Sciences, Lanzhou, Gansu Province (CN)

(72) Inventors: Feng Shi, Lanzhou (CN); Xinjiang Cui, Lanzhou (CN); Hangkong Yuan, Lanzhou (CN); Yan Zhang, Lanzhou (CN); Youquan Deng, Lanzhou (CN)

(73) Assignee: Lanxhou Institute of Chemical Physics, Chinese Academy of Sciences, Lanzhou (CN)

( * ) Notice: Subject to any disclaimer, the term of this patent is extended or adjusted under 35 U.S.C. 154(b) by 118 days.

(21) Appl. No.: 14/040,513

(22) Filed: Sep. 27, 2013

(65) Prior Publication Data
US 2015/0018548 A1    Jan. 15, 2015

(30) Foreign Application Priority Data
Jul. 9, 2013    (CN) .......................... 2013 1 0288088

(51) Int. Cl.
| | | |
|---|---|---|
| *C07D 295/023* | (2006.01) | |
| *C07D 295/03* | (2006.01) | |
| *C07D 295/033* | (2006.01) | |
| *C07C 209/60* | (2006.01) | |
| *C07C 209/68* | (2006.01) | |
| *C07C 211/46* | (2006.01) | |
| *C07C 211/48* | (2006.01) | |
| *C07C 211/55* | (2006.01) | |
| *C07C 213/08* | (2006.01) | |
| *B01J 23/72* | (2006.01) | |
| *C07D 211/14* | (2006.01) | |
| *C07C 209/26* | (2006.01) | |
| *C07C 209/36* | (2006.01) | |
| *C07C 209/48* | (2006.01) | |
| *C07C 213/02* | (2006.01) | |

(52) U.S. Cl.
CPC .......... *C07D 295/03* (2013.01); *C07C 209/26* (2013.01); *C07C 209/36* (2013.01); *C07C 209/48* (2013.01); *C07C 213/02* (2013.01); *C07C 213/08* (2013.01); *C07D 211/14* (2013.01)

(58) Field of Classification Search
CPC .............. C07D 295/023; C07D 295/03; C07D 295/033; C07C 209/60; C07C 209/68; C07C 211/46; C07C 211/48; C07C 211/55; C07C 213/08; B01J 23/72

USPC ........ 544/178, 579; 564/443, 305, 442, 428; 548/579, 429; 546/184
See application file for complete search history.

(56) References Cited

U.S. PATENT DOCUMENTS 3,822,271 A    7/1974   Laporte

FOREIGN PATENT DOCUMENTS

| RU | 2275353 C2 | 4/2006 |
|---|---|---|
| WO | WO200902044 A1 * | 2/2009 |

OTHER PUBLICATIONS

Gredig, S., R. Koeppel, and A. Baiker "Comparative study of synthesis of methylamines from carbon oxides and ammonia over Cu/Al2O3" Catalys Today (1996), 29: pp. 339-342.*
Auer, S., S. Gredig, R. Koppel, and A. Baiker "Synthesis of methylamines from CO2, H2, and NH3 over Cu—Mg—Al mixed oxides" Journ. Mol. Catal. (1999), 141 (1-3), pp. 193-203.*
Olivier Jacquet et al., $CO_2$ as a $C_1$-building block for the catalytic methylation of amine, Chem. Sci., vol. 4, pp. 2127-2131 (2013).
Yuehui Li et al., A General Catalytic Methylation of Amines Using Carbon Dioxide, Angew. Chem. Int. Ed. vol. 52, pp. 9568-9571 (2013).
Steffen M. Auer et al., Synthesis of methylamines from $CO_2$, $H_2$, and $NH_3$ over Cu—Mg—Al mixed oxides, Journal of Molecular Catalysis A: Chemial 141, 193-203 (1999).

* cited by examiner

*Primary Examiner* — Alicia L Otton
*Assistant Examiner* — Sagar Patel
(74) *Attorney, Agent, or Firm* — Mei & Mark LLP; Manni Li

(57) ABSTRACT

A process for producing N-methyl or N,N-dimethyl amines, which comprises using amine compound, nitro-containing compound or nitrile compound as a starting material, carbon dioxide as a methylating agent and hydrogen gas as a reducing agent, and allowing them to react in a sealed reactor for 6 to 48 h in a reaction medium at a reaction temperature of 80 to 180 ° C. in the presence of a composite catalyst, so as to provide N-methyl or N,N-dimethyl amines. The process of the present invention is simple and under relative mild reaction conditions. By means of the process of the invention, the target products can be prepared at low cost with a high yield. The catalysts used have a high catalytic activity and can be separated from the reaction system simply and reused. Furthermore, the whole process of the present invention is environmental-friendly and facilitates the cycling use of carbon dioxide.

8 Claims, No Drawings

PROCESS FOR PRODUCING N-METHYL OR N,N-DIMETHYL AMINES

CROSS-REFERENCE AND RELATED APPLICATION

The subject application claims priority on Chinese Patent Application CN 201310288088.7 filed on Jul. 9, 2013. The subject matter and contents of the priority application is incorporated herein by reference in the entirety.

TECHNICAL FIELD

The invention relates to a process for producing N-methyl or N,N-dimethyl amines. In particular, the present application relates to a process for producing N-methyl or N,N-dimethyl amines by using carbon dioxide as the methyl carbon source which is reduced and reacted with an amine compound to achieve amination.

BACKGROUND ART

N-methyl or N,N-dimethyl amines are important part of N-alkylated amines and widely used in the field of chemistry, chemical industry and pesticides production. For example, N-methylaniline can be used for producing novel pesticides and insecticides such as buprofezin, methyldimuron, anilinephenobenzuron, latifolinine etc.; for producing dye intermediates such as N-methyl-N-benzylaniline and N-methyl-N-hydroxyethylaniline etc.; for producing rubber ingredients such as zinc methylphenyldithioaminoformate, dithiodimethyldiphenylthiuram; and also for producing deterrent in nitroglycerin powder, i.e. N-methyl-N-phenylaminoformyl chloride. Also, typical N,N-dimethylaniline is useful for producing perfumes such as vanillin; basic dyes such as basic flavine, basic violet 5BN, basic turquoise blue BB etc., and key intermediates of sulfonylureas herbicide, such as 2-amino-4,6-dichloropyrimidine etc.

It is well known that amines can be produced at low cost on a large scale, and the modern industrial production techniques of amines have been established. At present, alkylation reaction of amines with methanol is a main production route of N-methyl or N,N-dimethyl amines and is widely used in the industrial production of N-methyl or N,N-dimethyl amines. As a regenerable source, carbon dioxide has a giant advantage, namely it has rich reserves and no toxicity. However, commercialization of this technique is limited by the current high cost and low efficiency in the chemical fixation technique of carbon dioxide. Since early 20th century, many studies have been performed on the chemical utilization of carbon dioxide and have achieved a series of progress. Among them, the most important chemical utilization process of carbon dioxide is the production of urea via the reaction between carbon dioxide and ammonia gas. In the meantime, carbon dioxide is also utilized well in the field of cyclic carbonate, polycarbonate materials production etc. Recently, the production of N-methylation or N,N-dimethylation is also achieved by using carbon dioxide as the methylating agent carbon source and silicanes as reducing agent (Chem. Sci., 2013, 4, 2127; Angew. Chem. Int. Ed., 2013, DOI: 10.1002/ anie.201301349). However, the use of silicanes as reducing agent results high production cost and difficult separation of the products, so that it cannot be applied on large scale. Hydrogen gas is currently the cleanest and cheapest reducing agent, thus the production of N-methyl or N,N-dimethyl amines by using carbon dioxide as the methylating carbon source and hydrogen gas as the reducing agent certainly has more excellent economical efficiency and environmental friendship.

Accordingly, for the purpose of industrial application, there is a strong need for developing a production process of N-methyl or N,N-dimethyl amines, in which carbon dioxide is used as the methylating carbon source and hydrogen gas as the reducing agent.

SUMMARY OF THE INVENTION

In view of the problems existed in the prior arts, an object of the present invention is to provide a novel process for producing N-methyl or N,N-dimethyl amines, in which N-methyl or N,N-dimethyl amines are synthesized by using carbon dioxide as a methylating agent and hydrogen gas as a reducing agent under a relative mild conditions in the presence of a composite catalyst.

To this end, the present invention provides a process for producing N-methyl or N,N-dimethyl amines comprising: using amine compound, nitro-containing compound or nitrile compound as a starting material, carbon dioxide as a methylating agent, and hydrogen gas as a reducing agent, and allowing them to react in a reaction medium in a sealed reactor for 6 to 48 h at a reaction temperature of 80 to 180° C. in the presence of a composite catalyst, to provide the N-methyl or N,N-dimethyl amines, wherein the composite catalyst is formed of oxides of at least two metals, or of oxide of at least one metal and at least another metal element, said metal or metal element is selected from the group consisting of aluminum, bismuth, zinc, tin, gold, silver, copper, nickel, palladium, platinum, iridium, rhodium, cobalt, iron, ruthenium, osmium, manganese, rhenium, chromium, molybdenum, tungsten, vanadium, titanium, zirconium, lanthanum, yttrium, cerium, magnesium, calcium and barium.

In a preferred aspect, the molar ratio of the methylating agent to the starting material is 1:1~20:1 and the molar ratio of the reducing agent to the starting material is 3:1~100:1.

In a preferred aspect, as the starting material, the amine compound is an aliphatic amine having a structure of $R^1$—$NH_2$,

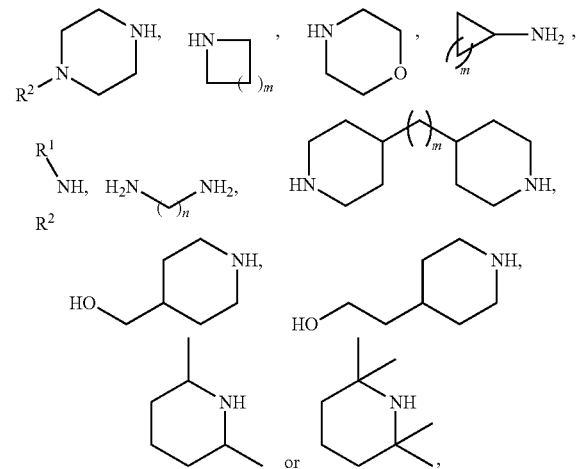

wherein $R^1$ and $R^2$ are each independently selected from hydrogen or $C_{1-18}$ alkyl, m is an integer of 1 to 6, and n is an integer of 1 to 12; or an aromatic amine having a structure of

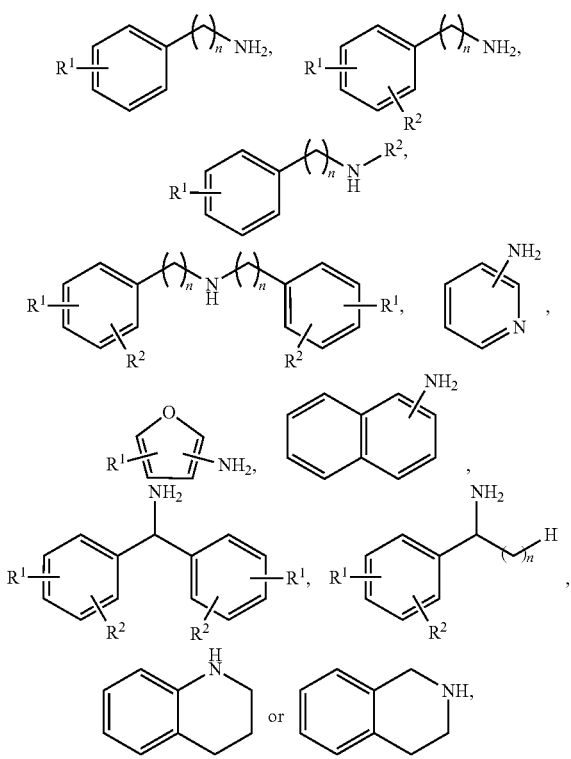

wherein $R^1$ and $R^2$ are each independently selected from hydrogen, $C_{1-18}$ alkyl, methoxy, phenyl, phenoxy, fluoro, chloro, bromo or iodo, and n is an integer of 0 to 12; the nitro-containing compound has a structure of

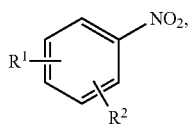

wherein $R^1$ and $R^2$ are each independently selected from hydrogen, $C_{1-18}$ alkyl, methoxy, phenyl, phenoxy, fluoro, chloro, bromo or iodo; the nitrile compound has a structure of

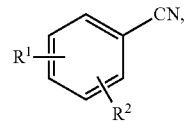

wherein $R^1$ and $R^2$ are each independently selected from hydrogen, $C_{1-18}$ alkyl, methoxy, phenyl, phenoxy, fluoro, chloro, bromo or iodo, and n is an integer of 0 to 12.

In a preferred aspect, the mass ratio of the composite catalyst to the starting material is 0.01:1~1.2:1.

In a preferred aspect, the composite catalyst is formed of oxides of at least two metals, or of oxide of at least one metal and at least another metal element, said metal or metal element is selected from the group consisting of aluminum, zinc, silver, copper, palladium, platinum, rhodium, cobalt, iron, ruthenium, manganese, zirconium and cerium.

In a preferred aspect, the reaction medium is at least one selected from water, toluene, xylene, trimethylbenzene, dioxane, tetrahydrofuran, n-hexane, n-octane and petroleum ether.

In a preferred aspect, the composite catalyst is produced as follows: to an aqueous solution of soluble salts of at least two metal selected from aluminum, bismuth, zinc, tin, gold, silver, copper, nickel, palladium, platinum, iridium, rhodium, cobalt, iron, ruthenium, osmium, manganese, rhenium, chromium, molybdenum, tungsten, vanadium, titanium, zirconium, lanthanum, yttrium, cerium, magnesium, calcium and barium, at least one select from aqueous solutions of alkali metal carbonate, alkali metal hydroxide, ammonia and urea is added as a co-precipitating agent, to provide a co-precipitate through co-precipitation; and the co-precipitate is washed, dried, calcinated and optionally reduced to provide the composite catalyst.

In a preferred aspect, the co-precipitation is carried out at room temperature for 1 to 5 h; the temperature for drying is 50 to 180° C. and the time for drying is 1 to 5 h; the temperature for calcinating is 200 to 800° C. and the time for calcinating is 5 to 15 h; and the temperature for reducing is 200 to 800° C. and the time for reducing is 1 to 5 h.

In a preferred aspect, the soluble salt is a nitrate or chloride of the metal, and the co-precipitating agent is at least one selected from aqueous solutions of NaOH, $Na_2CO_3$, KOH, $K_2CO_3$, $NH_3$ and urea.

In a preferred aspect, the obtained composite catalyst is formed of at least two oxides, or of at least one oxide and at least one metal element, said oxide or metal element is selected from aluminum sesquioxide, zinc oxide, silver, cupric oxide, cuprous oxide, copper, palladium, platinum, rhodium, ruthenium, cobalt, cobalt sesquioxide, cobaltosic oxide, cobalt monooxide, iron sesquioxide, zirconium dioxide, cerium dioxide and cerium sesquioxide.

When compared to the prior art, in the process for producing N-methyl or N,N-dimethyl amines of the invention, carbon dioxide is used as a methylating agent, and hydrogen gas as a reducing agent, which renders the present process economical, cheaper and environmental-friendly; the catalyst used can be produced easily and has a high catalytic efficiency; the production conditions are mild, and the catalyst is noncorrosive and can be easily separated and reused.

DETAILED DESCRIPTION OF THE INVENTION

In the process for producing N-methyl or N,N-dimethyl amines of the present invention, amine compound, carbon dioxide and hydrogen gas, or nitro-containing compound, carbon dioxide and hydrogen gas, or nitrile compound, carbon dioxide and hydrogen gas are used as the substrate, wherein the amine compound, nitro-containing compound or nitrile compound is used as a starting material, carbon dioxide is used as a methylating agent, and hydrogen gas is used as a reducing agent, and the N-methyl or N,N-dimethyl amines is synthesized by reacting the substrate in a sealed reactor for 6 to 48 h in a reaction medium at a temperature of 80 to 180° C. in the presence of a composite catalyst.

In the present invention, the term "N-methyl or N,N-dimethyl amines " refers to N-methyl primary amines or N,N-dimethyl secondary amines.

In the present invention, the term "composite catalyst" refers to a catalyst formed of two or more metal oxides, or of at least one metal oxide and at least another metal element. Preferably, the composite catalyst used is formed of oxides of at least two metals, or of oxide of at least one metal and at least another metal element, said metal or metal element is selected from the group consisting of aluminum, bismuth, zinc, tin, gold, silver, copper, nickel, palladium, platinum, iridium, rhodium, cobalt, iron, ruthenium, osmium, manganese, rhenium, chromium, molybdenum, tungsten, vanadium, titanium, zirconium, lanthanum, yttrium, cerium, magnesium, calcium and barium. A particularly preferred composite catalyst is formed of oxides of at least two metals, or of oxide of at least one metal and at least another metal element, said metal or metal element is selected from the group consisting of aluminum, zinc, silver, copper, palladium, platinum, rhodium, cobalt, iron, ruthenium, manganese, zirconium and cerium.

In the present invention, the composite catalyst used is preferably produced as follows: to an aqueous solution of soluble salts of at least two metal selected from aluminum, bismuth, zinc, tin, gold, silver, copper, nickel, palladium, platinum, iridium, rhodium, cobalt, iron, ruthenium, osmium, manganese, rhenium, chromium, molybdenum, tungsten, vanadium, titanium, zirconium, lanthanum, yttrium, cerium, magnesium, calcium and barium, at least one select from aqueous solutions of alkali metal carbonate, alkali metal hydroxide, ammonia and urea is added as a co-precipitating agent, to provide (e.g. via conventional filtration) a co-precipitate through co-precipitation; and the co-precipitate is washed, dried, calcinated and optionally reduced (e.g. by using hydrogen gas) to provide the composite catalyst.

For example, in a specific embodiment, the process for producing the composite catalyst comprises the following steps: to an aqueous solution of any two or three selected from aluminum nitrate, zinc nitrate, silver nitrate, copper nitrate, chloro-palladic acid, potassium chloro-palladate, chloroplatinic acid, rhodium chloride, cobalt nitrate, iron nitrate, ruthenium chloride, zirconium chloride, zirconium nitrate, cerium nitrate, cerium ammonium nitrate and cerium chloride, an aqueous solution of NaOH, $Na_2CO_3$, KOH, $K_2CO_3$, $NH_3$ or urea is added as a precipitator to perform co-precipitation; then the resulting co-precipitate is washed, dried in air, calcinated, and (optionally) reduced in hydrogen gas, so as to provide the composite catalyst. Preferably, the co-precipitation is carried out at room temperature (RT) for 1 to 5 h; the temperature for drying is 50 to 180° C. and the time for drying is 1 to 5 h; the temperature for calcinating is 200 to 800° C. and the time for calcinating is 5 to 15 h; and the temperature for reducing is 200 to 800° C. and the time for reducing is 1 to 5 h.

Preferably, the composite catalyst obtained by the above process is formed of at least two oxides, or of at least one oxide and at least one metal element, said oxide or metal element is selected from aluminum sesquioxide, zinc oxide, silver, cupric oxide, cuprous oxide, copper, palladium, platinum, rhodium, ruthenium, cobalt, cobalt sesquioxide, cobaltosic oxide, cobalt monooxide, iron sesquioxide, zirconium dioxide, cerium dioxide and cerium sesquioxide.

Furthermore, preferably, the weight ratio of the composite catalyst to the starting material (i.e. the amine compound, nitro-containing compound or nitrile compound) is 0.01: 1~1.2:1.

In the present invention, preferably, the molar ratio of carbon dioxide used as the methylating agent to the starting material (i.e. the amine compound, nitro-containing compound or nitrile compound) is 1:1~20:1. The carbon dioxide used in the present invention can be purchased directly from market.

The molar ratio of hydrogen gas used as the reducing agent to the starting material (i.e. the amine compound, nitro-containing compound or nitrile compound) is 3:1~100: 1. The hydrogen gas used in the present invention can be purchased directly from market.

In the present invention, preferably, the amine compound used as a starting material is an aliphatic amine having a structure of $R^1$—$NH_2$,

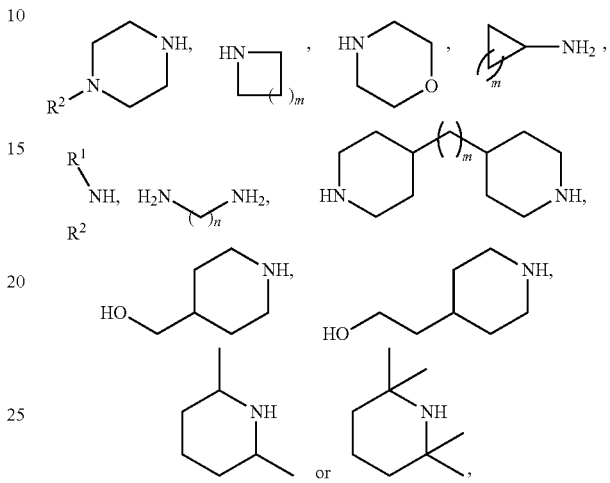

wherein $R^1$ and $R^2$ are each independently selected from hydrogen or $C_{1-18}$ alkyl, m is an integer of 1 to 6, and n is an integer of 1 to 12; or an aromatic amine having a structure of

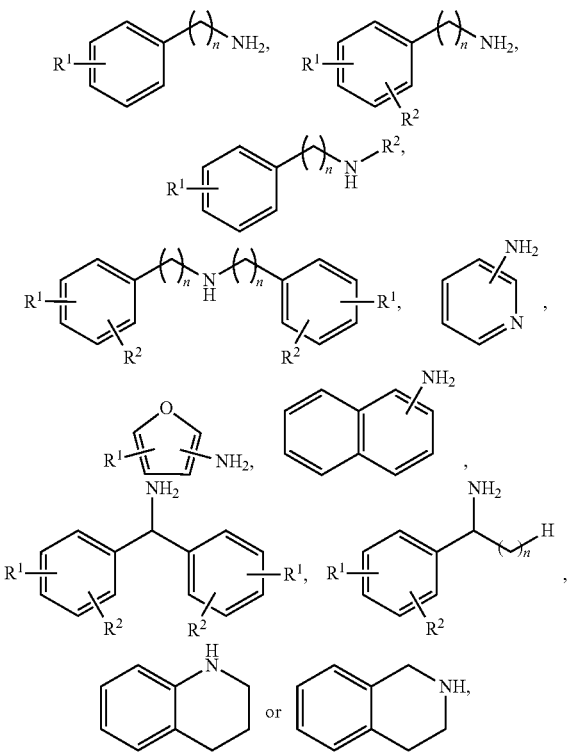

wherein $R^1$ and $R^2$ are each independently selected from hydrogen, $C_{1-18}$ alkyl, methoxy, phenyl, phenoxy, fluoro, chloro, bromo or iodo, and n is an integer of 0 to 12.

Preferably, the nitro-containing compound used as a starting material has a structure of

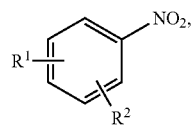

wherein R1 and R2 are each independently selected from hydrogen, C1-18 alkyl, methoxy, phenyl, phenoxy, fluoro, chloro, bromo or iodo, and n is an integer of 0 to 12.

Preferably, the nitrile compound used as a starting material has a structure of

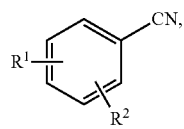

wherein $R^1$ and $R^2$ are each independently selected from hydrogen, $C_{1-18}$ alkyl, methoxy, phenyl, phenoxy, fluoro, chloro, bromo or iodo.

In the present invention, the reaction medium used is preferably at least one of water, toluene, xylene, trimethylbenzene, dioxane, tetrahydrofuran, n-hexane, n-octane, n-decane and petroleum ether.

In the present invention, the sealed container used can be a container which is known in the art and can be sealed to maintain a certain pressure therein, for example, an autoclave as used commonly in chemical reactions, which is typically equipped with heating or cooling devices such as water bath, oil bath or ice bath, as commonly used in the art, as well as supporting facilities for ventilating or emptying, such as gas bottle and pressure gauge, all of which are known to those skilled in the art.

EXAMPLES

Hereinafter, the invention is further illustrated by way of examples. However, it should be understood that these examples are merely used to exemplify the practice and effect of the present process, without limiting the scope of the invention in any way.

Preparation of Composite Catalyst

Example 1

1.45 g (6.0 mmol) copper nitrate trihydrate and 2.25 g (6 0 mmol) aluminum nitrate nonahydrate, both purchased commercially, were weighed and added into 100 mL deionized water, and magnetically stirred in a 200 mL round-bottom flask at ambient temperature. After the dissolution was completed, 20 mL of 0.94 mol/L aqueous $Na_2CO_3$ solution (as the co-precipitating agent) was added dropwise under stirring, and then the mixture was stirred at RT for 4 h. A centrifugation was performed by using a centrifuge (Shanghai Anting Scientific Apparatus Company) at 8000 rpm for 5 min. The co-precipitate was provided by separation, washed with deionized water until being neutral, dried at 120° C. for 4 h in an oven, and calcinated at 350° C. for 12 h in a muffle furnace. Then a reducing furnace was used with a programmed heating up to 350° C. at 10° C./min, the resulting product was reduced for 3 h under hydrogen atmosphere at 350° C. to yield a catalyst as black powder. The analysis results of XRD, XPS and TEM showed that the catalyst thus obtained was a $Cu-Al_2O_3$ composite, which was designated as Catalyst A.

Example 2

5.3 mg (0.05 mmol) palladium chloride was weighed and dissolved in an appropriate amount of concentrated hydrochloric acid, and then the solution was added into 50 mL distilled water together with 0.73 g (3.0 mmol) copper nitrate trihydrate and 0.43 g (1.0 mmol) zirconium nitrate pentahydrate. The mixture was magnetically stirred in a 100 mL round-bottom flask at ambient temperature. After the dissolution was completed, 20 mL of 0.47 mol/L aqueous $Na_2CO_3$ solution (as the co-precipitating agent) was added dropwise under stirring, and then the mixture was stirred at RT for 4 h. A centrifugation was performed by using a centrifuge (Shanghai Anting Scientific Apparatus Company) at 8000 rpm for 5 min. A co-precipitate was obtained by separation, washed with deionized water until being neutral, dried at 100° C. for 4 h in an oven, and calcinated at 350° C. for 6 h in a muffle furnace. Then a reducing furnace was used with a programmed heating up to 300° C. at 10° C./min, the resulting product was reduced for 3 h under hydrogen atmosphere at 300° C. to yield a catalyst as black powder. The analysis results of XRD, XPS and TEM showed that the catalyst thus obtained was a $Pd-Cu-ZrO_2$ composite, which was designated as Catalyst B.

Example 3

The procedure was same as that in Example 2, except that 0.05 mmol rhodium chloride was used in place of palladium chloride. A catalyst $Rh-Cu-ZrO_2$ was obtained and designated as Catalyst C.

Example 4

The procedure was same as that in Example 2, except that 0.05 mmol platinic chloride was used in place of palladium chloride. A catalyst $Pt-Cu-ZrO_2$ was obtained and designated as Catalyst D.

Example 5

The procedure was same as that in Example 2, except that 0.05 mmol ruthenium chloride was used in place of palladium chloride. A catalyst $Ru-Cu-ZrO_2$ was obtained and designated as catalyst E.

Example 6

The procedure was same as that in Example 2, except that 0.05 mmol iridium chloride was used in place of palladium chloride. A catalyst $Ir-Cu-ZrO_2$ was obtained and designated as Catalyst F

Example 7

The procedure was same as that in Example 2, except that 0.05 mmol silver nitrate was used in place of palladium chloride. A catalyst $Ag-Cu-ZrO_2$ was obtained and designated as Catalyst G

Example 8

The procedure was same as that in Example 2, except that 3 mmol cobalt nitrate was used in place of copper nitrate. A catalyst Pd—Co—ZrO$_2$ was obtained and designated as Catalyst H.

Example 9

The procedure was same as that in Example 6, except that 3 mmol zinc nitrate was used in place of copper nitrate. A catalyst Ir—ZnO—ZrO$_2$ was obtained and designated as Catalyst I.

Example 10

The procedure was same as that in Example 6, except that 3 mmol iron nitrate was used in place of copper nitrate. A catalyst Ir—Fe$_3$O$_4$—ZrO$_2$ was obtained and designated as Catalyst J.

Example 11

The procedure was same as that in Example 6, except that 3 mmol cerium nitrate was used in place of copper nitrate. A catalyst Ir—CeO$_2$—ZrO$_2$ was obtained and designated as catalyst K.

Example 12

The procedure was same as that in Example 2, except that 25 mL of 1.7 mol/L aqueous potassium carbonate solution was used in place of aqueous sodium carbonate solution. A catalyst Pd—Cu—ZrO$_2$ was obtained and designated as Catalyst L.

Example 13

The procedure was same as that in Example 2, except that 25 mL of 25 wt % concentrated ammonia was used in place of aqueous sodium carbonate solution. A catalyst Pd—Cu—ZrO$_2$ was obtained and designated as Catalyst M.

Example 14

The procedure was same as that in Example 2, except that 25 mL of 2 mol/L aqueous urea solution was used in place of aqueous sodium carbonate solution. A catalyst Pd—Cu—ZrO$_2$ was obtained and designated as Catalyst N.

Example 15

The procedure was same as that in Example 2, except that 25 mL of 2 mol/L aqueous sodium hydroxide solution was used in place of aqueous sodium carbonate solution. A catalyst Pd—Cu—ZrO$_2$ was obtained and designated as Catalyst O.

Example 16

5.3 mg (0.05 mmol) palladium chloride was weighed and dissolved in an appropriate amount of concentrated hydrochloric acid, and then the solution was added into 50 mL distilled water together with 0.89 g (3.0 mmol) zinc nitrate hexahydrate, 0.43 g (1.0 mmol) zirconium nitrate pentahydrate and 1.125 g (3 0 mmol) aluminum nitrate nonahydrate. The mixture was magnetically stirred in a 100 mL round-bottom flask at ambient temperature. After the dissolution was completed, 30 mL of 0.47 mol/L aqueous Na$_2$CO$_3$ solution (as the co-precipitating agent) was added dropwise under stirring, and then the mixture was stirred at RT for 4 h. A centrifugation was performed by using a centrifuge (Shanghai Anting Scientific Apparatus Company) at 8000 rpm for 5 min. A co-precipitate was obtained by separation, washed with deionized water until being neutral, dried at 100° C. for 4 h in an oven, and calcinated at 350° C. for 6 h in a muffle furnace. Then a reducing furnace was used with a programmed heating up to 300° C. at 10° C./min, the resulting product was reduced for 3 h under hydrogen atmosphere at 300° C. to yield a catalyst as black powder. The analysis results of XRD, XPS and TEM showed that the catalyst was a Pd—ZnO—ZrO$_2$—Al$_2$O$_3$ composite, which was designated as Catalyst P.

Example 17

0.873 g (3 mmol) cobalt nitrate hexahydrate and 1.125 g (3 0 mmol) aluminum nitrate nonahydrate were weighed and added together into 50 mL distilled water. The mixture was magnetically stirred in a 100 mL round-bottom flask at ambient temperature. After the dissolution was completed, 40 mL of 0.47 mol/L aqueous Na$_2$CO$_3$ solution (acting as co-precipitating agent) was added dropwise under stirring, and then the mixture was stirred at RT for 4 h. A centrifugation was performed by using a centrifuge (Shanghai Anting Scientific Apparatus Company) at 8000 rpm for 5 min. A co-precipitate was obtained by separation, washed with deionized water until being neutral, dried at 100° C. for 4 h in an oven, and calcinated at 350° C. for 6 h in a muffle furnace. Then a reducing furnace was used with a programmed heating up to 200° C. at 10° C./min, the resulting product was reduced for 3 h under hydrogen atmosphere at 200° C. to yield a catalyst as black powder. The analysis results of XRD, XPS and TEM showed that the catalyst was a CoO—Al$_2$O$_3$ composite, which was designated as Catalyst Q.

Example 18

0.89 g (3.0 mmol) zinc nitrate hexahydrate, 1.125 g (3.0 mmol) aluminum nitrate nonahydrate and 1.21 g (3 mmol) iron nitrate nonahydrate were weighed and added together into 50 mL distilled water. The mixture was magnetically stirred in a 100 mL round-bottom flask at ambient temperature. After the dissolution was completed, 40 mL of 0.47 mol/L aqueous Na$_2$CO$_3$ solution (as the co-precipitating agent) was added dropwise under stirring, and then the mixture was stirred at RT for 4 h. A centrifugation was performed by using a centrifuge (Shanghai Anting Scientific Apparatus Company) at 8000 rpm for 5 min. A co-precipitate was obtained by separation, washed with deionized water until being neutral, dried at 100° C. for 4 h in an oven and calcinated at 350° C. for 6 h in a muffle furnace. Then a reducing furnace was used with a programmed heating up to 300° C. at 10° C./min, the resulting product was reduced for 3 h under hydrogen atmosphere at 300° C. to yield a catalyst as black powder. The analysis results of XRD, XPS and TEM showed that the catalyst was a ZnO—Fe$_3$O$_4$—Al$_2$O$_3$ composite, which was designated as Catalyst R.

Production of N-methyl or N,N-methyl Amines

Example 19

50 mg Catalyst A prepared in Example 1 was weighed and added into a 100 mL self-made autoclave with magnetic stirring. Then 93 mg (1 mmol) aniline and 2 mL n-octane were added. The inside of the autoclave was replaced by carbon dioxide gas for three times. Then carbon dioxide gas was charged until the inner pressure of the autoclave was reached 3.0 MPa, and hydrogen gas was further charged until the inner pressure of the autoclave was reached 7.0 MPa. Thereafter, the autoclave was heated up to 150° C. with an electric heating furnace and maintained at this temperature for 24 h. Then the autoclave was cooled to RT by means of water cooling. A centrifugation was performed by using a centrifuge (Shanghai Anting Scientific Apparatus Company) at 8000 rpm for 5 min. Catalyst A was recovered from the reaction mixture solution by separation. The reaction mixture was subject to a qualitative analysis with HP 6890/5973 GC-MS gas-mass chromatograph to detect the resulting target product, N-methylaniline, and N-methylaniline standard product was used for comparison. The reaction mixture was subjected to a quantitative analysis with Agilent 7890A gas-mass chromatograph (30 m×0.25 mm×0.33 μm capillary column, with hydrogen flame ionization detector), and diphenyl was used as an internal standard. The target product, N-methylaniline, was obtained by the methods well known in the art, such as the industrial rectification method. The yield of the product was shown in Table 1 below.

Examples 20-36

The procedure was same as that in Example 19, except that Catalysts B, C, D, E, F, G, H, I, J, K, L, M, N, O, P, Q and R were used in place of Catalyst A, respectively. The results were shown in Table 1 below.

Examples 37-45

The procedure was same as that in Example 19, except that water, toluene, xylene, trimethylbenzene, dioxane, tetrahydrofuran, n-hexane, n-decane and petroleum ether (60-90° C.) were used in place of n-octane. The results were shown in Table 1 below.

TABLE 1

| Example | Catalyst | Reaction Medium | Yield (%) |
|---|---|---|---|
| 19 | A | n-octane | 86 |
| 20 | B | n-octane | 92 |
| 21 | C | n-octane | 87 |
| 22 | D | n-octane | 83 |
| 23 | E | n-octane | 86 |
| 24 | F | n-octane | 81 |
| 25 | G | n-octane | 83 |
| 26 | H | n-octane | 80 |
| 27 | I | n-octane | 59 |
| 28 | J | n-octane | 75 |
| 29 | K | n-octane | 29 |
| 30 | L | n-octane | 79 |
| 31 | M | n-octane | 82 |
| 32 | N | n-octane | 81 |
| 33 | O | n-octane | 70 |
| 34 | P | n-octane | 64 |
| 35 | Q | n-octane | 72 |
| 36 | R | n-octane | 10 |
| 37 | A | water | 75 |
| 38 | A | toluene | 80 |
| 39 | A | xylene | 71 |
| 40 | A | trimethylbenzene | 73 |
| 41 | A | dioxane | 62 |
| 42 | A | tetrahydrofuran | 66 |

TABLE 1-continued

| Example | Catalyst | Reaction Medium | Yield (%) |
|---|---|---|---|
| 43 | A | n-hexane | 83 |
| 44 | A | n-decane | 83 |
| 45 | A | petroleum ether (60-90° C.) | 82 |

The results in Table 1 showed that, in the present invention, N-methyl or N,N-dimethyl amines, as the target products, were produced by using amine compound as a starting material, carbon dioxide as a methylating agent and hydrogen gas as a reducing agent, and performing a reaction in a reaction medium in the presence of the catalysts prepared, wherein the yield was up to 90% or more. Furthermore, all of the catalysts prepared in the present invention have a higher catalytic activity in the above reaction. In addition, the results in Table 1 also showed that the reaction of the present invention can be performed in various reaction media.

Reuse of the Catalysts

Example 46

The Catalyst A recovered from Example 19 was centrifuged in a centrifuge (Shang Anting Scientific Apparatus Factory) for 5 min at 8000 rpm, and then separated, washed with n-octane at RT and centrifuged again. This procedure was repeated three times. The process of Example 19 was performed again with the Catalyst A thus recovered. The reaction mixture was subject to a qualitative analysis with HP 6890/5973 GC-MS gas-mass chromatograph. The resulting target product was N-methylaniline. The reaction mixture was subjected to a quantitative analysis with Agilent 7890A gas-mass chromatograph (30 m×0.25 mm×0.33 μm capillary column, with a hydrogen flame ionization detector), and diphenyl was used as an internal standard. The target product N-methylaniline was obtained by the methods well known in the art, such as the industrial rectification method. The yield of the prepared N-methylaniline was 81%.

Furthermore, the above reused Catalyst A was subjected to a recovery treatment by the procedure same with above. Then the procedure of Example 19 was performed again with such recovered Catalyst A once more. The reaction mixture was subject to a qualitative analysis with HP 6890/5973 GC-MS gas-mass chromatograph, and a N-methylaniline standard product was used for comparison. The resulting target product was N-methylaniline. The reaction mixture was subjected to a quantitative analysis with Agilent 7890A gas-mass chromatograph (30 m×0.25 mm×0.33 μm capillary column, with a hydrogen flame ionization detector), and diphenyl was used as an internal standard. The target product, N-methylaniline, was obtained by the methods well known in the art, such as the industrial rectification method. The yield of the prepared N-methylaniline was 82%.

From the above results, it can be seen that the composite catalyst prepared in the present invention can be reused, and in the reuse, it still has equivalent catalytic activity as to that in the initial use.

In addition, investigation was perform on the reuse of the other Catalysts B, C, D, E, F, G, H, I, J, K, L, M, N, O, P, Q and R prepared above. The results are similar to those of Catalyst A. That is, when reused many times, these catalysts still have equivalent catalytic activity to that in the initial use thereof, respectively.

Use of Different Starting Materials

Examples 47-82

The procedures were same as that in Example 19. In a 100 mL reaction autoclave with magnetic stirring, 50 mg Catalyst A was used. The reaction medium was 2 mL n-hexane. 1 mmol starting material was added respectively. After being sealed, the inside of the autoclave was replaced by carbon dioxide gas for three times. Then carbon dioxide gas and hydrogen gas were charged, wherein the starting material, the pressure of the autoclave after charging carbon dioxide and hydrogen gas ($P_{CO2}$ and $P_{H2}$, respectively), reaction temperature, reaction time and target products (qualitative analysis and detection were similar to those in Example 46) were shown in Table 2 below, respectively. After stopping the reaction and cooling to RT, the reaction mixture was subjected to a quantitative analysis with Agilent 7890A gas-mass chromatograph (30 m×0.25 mm×0.33 μm capillary column, with a hydrogen flame ionization detector). The target products were obtained by the conventional separation and purification methods well known in the art, such as rectification. The yields of the target products were shown in Table 2 below.

TABLE 2

| Examples | Temperature (° C.) | Time (h) | $P_{CO2}/P_{H2}$ (MPa) | Starting material | Target product | Yield (%) |
|---|---|---|---|---|---|---|
| 47 | 160 | 24 | 3.0/6.0 | 4-methylaniline | N-methyl-4-methylaniline | 79 |
| 48 | 160 | 24 | 3.0/6.0 | 4-methoxyaniline | N-methyl-4-methoxyaniline | 80 |
| 49 | 160 | 24 | 3.0/6.0 | 4-chloroaniline | N-methyl-4-chloroaniline | 65 |
| 50 | 160 | 24 | 3.0/6.0 | 2-aminobiphenyl | N-methyl-2-aminobiphenyl | 80 |
| 51 | 160 | 24 | 3.0/6.0 | 2-naphthylamine | N-methyl-2-naphthylamine | 70 |
| 52 | 160 | 24 | 3.0/6.0 | $C_{11}H_{23}CH_2NH_2$ | $C_{11}H_{23}CH_2NHCH_3$ | 43 |
| 53 | 160 | 48 | 3.0/7.0 | aniline | N,N-dimethylaniline | 83 |
| 54 | 160 | 48 | 3.0/7.0 | 4-methylaniline | N,N-dimethyl-4-methylaniline | 80 |
| 55 | 160 | 48 | 3.0/7.0 | 4-methoxyaniline | N,N-dimethyl-4-methoxyaniline | 85 |

TABLE 2-continued

| Examples | Temperature (° C.) | Time (h) | $P_{CO2}/P_{H2}$ (MPa) | Starting material | Target product | Yield (%) |
| --- | --- | --- | --- | --- | --- | --- |
| 56 | 160 | 48 | 3.0/7.0 | 4-chloroaniline | N,N-dimethyl-4-chloroaniline | 64 |
| 57 | 160 | 48 | 3.0/7.0 | benzylamine | N,N-dimethylbenzylamine | 81 |
| 58 | 160 | 48 | 3.0/7.0 | 4-methylbenzylamine | N,N-dimethyl-4-methylbenzylamine | 71 |
| 59 | 160 | 48 | 3.0/7.0 | 4-methoxybenzylamine | N,N-dimethyl-4-methoxybenzylamine | 75 |
| 60 | 160 | 48 | 3.0/7.0 | 4-isopropylbenzylamine | N,N-dimethyl-4-isopropylbenzylamine | 83 |
| 61 | 160 | 24 | 3.0/7.0 | N-methylaniline | N,N-dimethylaniline | 86 |
| 62 | 160 | 24 | 3.0/7.0 | N-methylbenzylamine | N,N-dimethylbenzylamine | 89 |
| 63 | 160 | 24 | 3.0/7.0 | dibenzylamine | N-methyldibenzylamine | 91 |
| 64 | 160 | 24 | 3.0/7.0 | di-n-heptylamine ($C_7H_{15}$-NH-$C_7H_{15}$) | N-methyl-di-n-heptylamine | 45 |
| 65 | 160 | 24 | 3.0/7.0 | pyrrolidine | N-methylpyrrolidine | 79 |
| 66 | 160 | 24 | 3.0/7.0 | 4-methylpiperidine | 1,4-dimethylpiperidine | 83 |
| 67 | 160 | 24 | 3.0/7.0 | piperidine | N-methylpiperidine | 87 |
| 68 | 160 | 24 | 3.0/7.0 | 1-methylpiperazine | 1,4-dimethylpiperazine | 84 |

TABLE 2-continued

| Examples | Temperature (° C.) | Time (h) | $P_{CO2}/P_{H2}$ (MPa) | Starting material | Target product | Yield (%) |
| --- | --- | --- | --- | --- | --- | --- |
| 69 | 160 | 24 | 3.0/7.0 | 1-ethylpiperazine | 1-ethyl-4-methylpiperazine | 92 |
| 70 | 160 | 24 | 3.0/7.0 | morpholine | 4-methylmorpholine | 86 |
| 71 | 160 | 24 | 3.0/7.0 | 1,3-di(piperidin-4-yl)propane | 1,3-bis(1-methylpiperidin-4-yl)propane | 79 |
| 72 | 160 | 24 | 3.0/7.0 | 1,2,3,4-tetrahydroisoquinoline | 2-methyl-1,2,3,4-tetrahydroisoquinoline | 96 |
| 73 | 170 | 24 | 3.0/7.0 | 2,6-dimethylpiperidine | 1,2,6-trimethylpiperidine | 72 |
| 74 | 170 | 24 | 3.0/7.0 | 2,2,6,6-tetramethylpiperidine | 1,2,2,6,6-pentamethylpiperidine | 83 |
| 75 | 170 | 24 | 3.0/7.0 | 4-(hydroxymethyl)piperidine | (1-methylpiperidin-4-yl)methanol | 65 |
| 76 | 170 | 24 | 3.0/7.0 | 2-(piperidin-4-yl)ethanol | 2-(1-methylpiperidin-4-yl)ethanol | 73 |
| 77 | 170 | 48 | 3.0/7.0 | nitrobenzene | N,N-dimethylaniline | 86 |
| 78 | 170 | 48 | 3.0/7.0 | 4-nitrotoluene | N,N,4-trimethylaniline | 79 |
| 79 | 170 | 48 | 3.0/7.0 | 4-methoxynitrobenzene | 4-methoxy-N,N-dimethylaniline | 86 |

TABLE 2-continued

| Examples | Temperature (° C.) | Time (h) | $P_{CO2}/P_{H2}$ (MPa) | Starting material | Target product | Yield (%) |
|---|---|---|---|---|---|---|
| 80 | 170 | 48 | 3.0/7.0 | biphenyl-NO₂ | biphenyl-HN-CH₃ | 83 |
| 81 | 170 | 48 | 3.0/7.0 | PhCN | PhCH₂N(CH₃)₂ | 55 |
| 82 | 170 | 48 | 3.0/7.0 | 4-MeO-C₆H₄-CN | 4-MeO-C₆H₄-CH₂N(CH₃)₂ | 45 |

The results in Table 2 showed that, in the present method, a reaction was performed by using various amine compounds, nitro-containing compounds or nitrile compounds as starting materials, carbon dioxide as the methylating agent and hydrogen gas as the reducing agent in a reaction medium in the presence of a composite catalyst prepared, the corresponding target products, N-methyl or N,N-dimethyl amines, can be prepared. The yield was even up to 95% or more.

Furthermore, in the present invention, corresponding target products, N-methyl or N,N-dimethyl amines, were also prepared by using other Catalysts B, C, D, E, F, G, H, I, J, K, L, M, N, O, P, Q and R above, and performing the reaction with different starting materials such as amine compounds, nitro-containing compounds or nitrile compounds, different temperatures, different pressures and different times. The results (not showed) were similar to those of the above Catalyst A.

In the present invention, the target products, N-methyl or N,N-dimethyl amines, are prepared simply and conveniently by using carbon dioxide as the methylating carbon source, hydrogen gas as the reducing agent, various starting materials selected from amine compounds, nitro-containing compounds or nitrile compounds as the substrate. The whole process is economical, cheap and environmental-friendly. The catalysts used can be prepared simply and cheaply, and have a high catalytic activity. The reaction conditions are relatively mild. The catalysts are noncorrosive, and can be separated easily and reused. Therefore, the present process has a wide prospect for industrial production.

It should be noted that it is obvious for those skilled in the art to make various modifications on these Examples, without departing the principle and spirit of the invention. Such modifications should be regarded in the protection scope of the present invention.

We claim:

1. A process for producing a primary or a secondary methylated N-methyl or N,N-dimethyl amines comprising reacting a primary or a secondary amine compound as a starting material, carbon dioxide as a methylating agent, and hydrogen gas as a reducing agent in a reaction medium in a sealed reactor for 6 to 48 hours at a reaction temperature of 80° C. to 180° C. in the presence of a composite catalyst to provide the primary or the secondary methylated N-methyl or N,N-dimethyl amines, wherein the composite catalyst is formed of oxides of at least two metals, or of an oxide of at least one metal and at least another metal element, each of said metals or metal element is selected from the group consisting of aluminum, bismuth, zinc, tin, gold, silver, copper, nickel, palladium, platinum, iridium, rhodium, cobalt, iron, ruthenium, osmium, manganese, rhenium, chromium, molybdenum, tungsten, vanadium, titanium, zirconium, lanthanum, yttrium, cerium, magnesium, calcium, and barium, wherein the primary or secondary amine compound is an aliphatic amine having a structure of

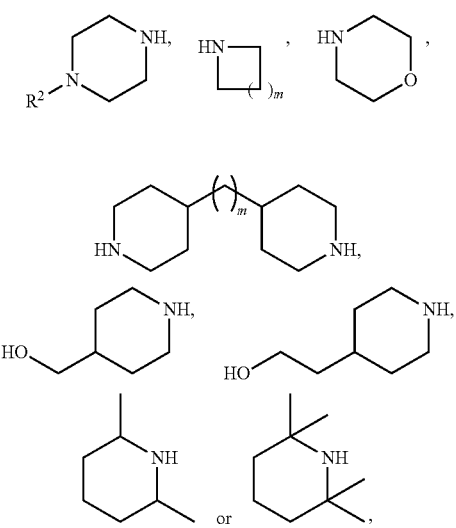

wherein $R^2$ is selected from the group consisting of hydrogen and $C_1$ alkyl to $C_{18}$ alkyl, m is an integer of 1 to 6, and n is an integer of 1 to 12; or the primary or secondary amine compound is an aromatic amine having a structure of

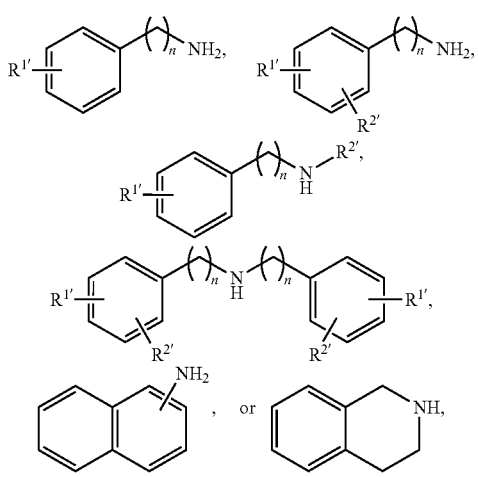

wherein $R^{1'}$ and $R^{2'}$ are each independently selected from hydrogen, $C_{1-18}$ alkyl, methoxy, phenyl, phenoxy, fluoro, chloro, bromo, or iodo, and n is an integer of 0 to 12.

2. The process according to claim 1, wherein the mass ratio of the composite catalyst to the starting material is 0.01:1~1.2:1.

3. The process according to claim 1, wherein the composite catalyst is formed of oxides of at least two metals, or of oxide of at least one metal and at least another metal element, said metal or metal element is selected from the group consisting of aluminum, zinc, silver, copper, palladium, platinum, rhodium, cobalt, iron, ruthenium, manganese, zirconium and cerium.

4. The process according to claim 1, wherein the reaction medium is selected from the group consisting of water, toluene, xylene, trimethylbenzene, dioxane, tetrahydrofuran, n-hexane, n-octane, petroleum ether, and a combination thereof.

5. The process according to claim 1, further comprising preparing the composite catalyst by adding ammonia and urea as a co-precipitating agent to an aqueous solution of soluble salts of at least two metals, the metals are selected from the group consisting of aluminum, bismuth, zinc, tin, gold, silver, copper, nickel, palladium, platinum, iridium, rhodium, cobalt, iron, ruthenium, osmium, manganese, rhenium, chromium, molybdenum, tungsten, vanadium, titanium, zirconium, lanthanum, yttrium, cerium, magnesium, calcium, and barium, and the aqueous solution is an aqueous solution of alkali metal carbonate or alkali metal hydroxide, and obtaining a co-precipitate through co-precipitation; and washing, drying, calcinating, and optionally reducing the co-precipitate to the composite catalyst.

6. The process according to claim 5, wherein the co-precipitation is carried out at room temperature for 1 to 5 h; the temperature for drying is 50 to 180° C. and the time for drying is 1 to 5 h; the temperature for calcinating is 200 to 800° C. and the time for calcinating is 5 to 15 h; and the temperature for reducing is 200 to 800° C. and the time for reducing is 1 to 5 h.

7. The process according to claim 5, wherein each of the soluble salts is a nitrate or chloride of the metal, and the co-precipitating agent is an aqueous solution of at least one selected from the group consisting of NaOH, $Na_2CO_3$, KOH, $K_2CO_3$, $NH_3$, and urea.

8. The process according to claim 5, wherein the composite catalyst is formed of at least two oxides, or of at least one oxide and at least one metal element, said oxide or metal element is selected from the group consisting of aluminum sesquioxide, zinc oxide, silver, cupric oxide, cuprous oxide, copper, palladium, platinum, rhodium, ruthenium, cobalt, cobalt sesquioxide, cobaltosic oxide, cobalt monoxide, iron sesquioxide, zirconium dioxide, cerium dioxide, and cerium sesquioxide.

* * * * *

UNITED STATES PATENT AND TRADEMARK OFFICE
CERTIFICATE OF CORRECTION

PATENT NO. : 9,688,646 B2  
APPLICATION NO. : 14/040513  
DATED : June 27, 2017  
INVENTOR(S) : Feng Shi et al.

Page 1 of 1

It is certified that error appears in the above-identified patent and that said Letters Patent is hereby corrected as shown below:

On the Title Page

Left Column, Line 11, item "(73) Assignee", the first word in the name of the assignee shall be changed from "Lanxhou" to --Lanzhou--.

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*